United States Patent
Thompson et al.

(10) Patent No.: US 10,657,179 B2
(45) Date of Patent: May 19, 2020

(54) BIPARTITE GRAPH STRUCTURE

(71) Applicant: X Development LLC, Mountain View, CA (US)

(72) Inventors: Jason Thompson, Redwood City, CA (US); Frank Russo, Sunnyvale, CA (US)

(73) Assignee: X DEVELOPMENT LLC, Mountain View, CA (US)

( * ) Notice: Subject to any disclaimer, the term of this patent is extended or adjusted under 35 U.S.C. 154(b) by 317 days.

(21) Appl. No.: 15/694,506

(22) Filed: Sep. 1, 2017

(65) Prior Publication Data

US 2019/0073433 A1    Mar. 7, 2019

(51) Int. Cl.

| | |
|---|---|
| *G06F 16/90* | (2019.01) |
| *G06F 16/901* | (2019.01) |
| *G16B 5/00* | (2019.01) |
| *G16B 45/00* | (2019.01) |
| *G16C 20/90* | (2019.01) |
| *G16B 50/00* | (2019.01) |

(Continued)

(52) U.S. Cl.
CPC ........... *G06F 16/9024* (2019.01); *G16B 5/00* (2019.02); *G16B 45/00* (2019.02); *G16B 50/00* (2019.02); *G16C 20/90* (2019.02); *G16C 10/00* (2019.02); *G16C 20/10* (2019.02)

(58) Field of Classification Search
CPC ...... G06F 16/9024; G16B 45/00; G16C 20/90
See application file for complete search history.

(56) References Cited

U.S. PATENT DOCUMENTS

| | | |
|---|---|---|
| 5,930,154 A | 7/1999 | Thalhammer-Reyero |
| 2005/0042663 A1* | 2/2005 | Blinov ...................... G16B 5/00 435/6.18 |
| 2007/0212719 A1* | 9/2007 | Hlavacek ................. G16B 5/00 435/6.14 |

FOREIGN PATENT DOCUMENTS

| | | |
|---|---|---|
| EP | 1494160 A2 | 1/2005 |
| WO | WO 2014/015196 A2 | 1/2014 |
| WO | WO2014/037914 A2 | 3/2014 |

OTHER PUBLICATIONS

PCT International Search Report and Written Opinion, PCT Application No. PCT/US2018/039129, dated Oct. 30, 2018, 15 pages.

(Continued)

*Primary Examiner* — Loc Tran
(74) *Attorney, Agent, or Firm* — Kilpatrick Townsend & Stockton LLP (57) ABSTRACT

A bipartite graph structure is utilized to better store data. The bipartite graph structure may be used in a biochemical database to efficiently store a variety of molecules and processes that might occur between the molecules. Molecules are represented as molecule nodes, which may have metadata fields including a molecule name, a molecule type, a molecular formula, a sequence, a molecular charge, a set of molecular properties, and a set of component molecules. Processes operating on the molecules are represented by process nodes, which may have metadata fields including a process name, a set of process roles, a set of process properties, and a set of sub-processes. Edges, called roles, each associate a molecule node with a process node and represent the role the associated molecule plays in the associated process. The roles may contain metadata identifying the role type and the stoichiometry coefficient of the molecule in the process.

19 Claims, 5 Drawing Sheets

(51) Int. Cl.
*G16C 20/10* (2019.01)
*G16C 10/00* (2019.01)

(56) References Cited

OTHER PUBLICATIONS

International Application No. PCT/US2018/039129, "International Preliminary Report on Patentability", dated Mar. 12, 2020, 10 pages.

* cited by examiner

Fig. 1

Molecule Node Examples

| Oxaloacetic Acid 200 | Water 214 | Citrate Synthase 228 |
|---|---|---|
| Type 202: compound | Type 216: inorganic compound | Type 230: protein |
| Molecular Formula 204: $HO_2CC(O)CH_2CO_2H$ | Molecular Formula 218: $H_2O$ | Molecular Formula 232: N/A |
| Sequence 206: N/A | Sequence 220: N/A | Sequence 234: ASSTNLK...IKLVDSK |
| Charge 208: 0 | Charge 222: 0 | Charge 236: Variable |
| Properties 210:<br><br>Molar mass: 132.07 g/mol<br>Density: 0.18 g/cm3<br>Melting point: 434 K<br>Standard enthalpy of formation: -943.21 kJ/mol<br>$pK_a$: 3.89 | Properties 224:<br><br>Molar mass: 18.02 g/mol<br>Density: 1 g/cm3<br>Melting point: 273.15 K | Properties 238:<br><br>Active Site: ...<br>Structures: ...<br>pH optimum: ...<br>Kinetics: ... |
| Component Molecules 212: Oxaloacetate, Proton | Component Molecules 226: N/A | Component Molecules 240: Amino acids: N/A |

*Fig. 2*

Process Node Examples

Citrate Synthase Reaction 300

Roles 302:
Substrates: $H_2O$, Acetyl-CoA, Oxaloacetate
Catalysts: Citrate Synthase
Products: H+, CoA, Citrate Properties 304:
Gibbs free energy change: -53.9 kJ/mol
....

Sub-processes 306:
Acetyl-CoA Enol Generation,
Citrate Generation

Endoplasmic Reticulum to Mitochondria Vesicle Transport 308

Roles 310:
Departure Molecule: Protein X (ER)
Arrival Molecule: Protein X (Mitochondria)

Properties 312:
Average transport rate: ...
....

Sub-processes 314:
Vesicle secretion, Mitochondrial vesicle fusion

BIPARTITE GRAPH STRUCTURE

TECHNICAL FIELD

This application relates generally to the curation and structure of stored data and efficient uses thereof.

BACKGROUND

Typically, information is stored in relational databases detailing relationships between multiple objects in a database. However, this information may be more efficiently stored in a bipartite graph structure.

SUMMARY

A description of a bipartite graph structure for efficiently storing data is disclosed herein. An example use of the bipartite graph structure is as a bipartite biochemical database for representing biochemical information, which is organized as a bipartite graph containing two categories of nodes: molecules and processes. Each molecule node represents a molecule, or chemical element that is utilized by one or more biochemical processes. A molecule node may represent small molecules such as water, carbon dioxide, protons, etc. or macromolecules such as DNA, RNA, and proteins. A molecule node contains a plurality of metadata fields describing the molecule including but not limited to a molecule name, a molecular formula, nucleic acid sequence, amino acid sequence, macromolecular structure, chemical modifications (such as methylation, phosphorylation etc.), electrical charge, chemical or physical properties (pKa, melting point, solubility etc.), and component molecules. Additionally, some non-physical properties may be included in the metadata for a molecule node including pathway information, drug interaction, 3D structures etc. A molecule node need not contain information for each one of the previously described metadata fields. Instead, each molecule is described using the fields that are pertinent to the molecule's interaction in a biochemical environment. For example, small molecules are best described by their chemical compositions and so the fields for nucleic acid sequence and macromolecular structure would not be applicable. On the other hand, a protein acting as an enzyme catalyst might contain information in the macromolecular structure, amino acid sequence, and binding site fields while not containing composition information as it may be variable or unimportant to the molecules function in a biochemical environment.

Process nodes describe molecular actions in a biochemical environment including but not limited to chemical reactions, regulatory interactions, binding, transport, or others. Like a molecule node, a process node includes a number of descriptive metadata fields that provide information about the process including but not limited to a list of molecules and their associated roles in the process, reaction rate information, and energy requirements for the process, sub-processes that may be involved in the process, or other more detailed information.

In addition to the molecule and process nodes, the biochemical database contains edges between the nodes that define the role of each molecule in each process and the stoichiometric coefficient assigned to that role. Each edge associates a molecule node with a process node thereby defining the bipartite structure of the database. Each edge also contains additional metadata characterizing the role of the associated molecule in the associated process. Any relevant characterization is possible including but not limited to reactant/substrate, catalyst, product, or cofactor.

The structure of the biochemical database lends itself to efficient methods for determining molecular interactions in a defined biochemical environment or determining a biochemical environment needed for a particular set of molecular interactions. For example, by selecting a set of molecule nodes that define a biochemical environment and traversing the bipartite graph, the set of biochemical interactions that are likely to occur in the biochemical environment can be determined. Alternatively, a set of desired process nodes can be selected and, by traversing the graph, the corresponding set of molecules that play a role in the selected set of processes can be determined. More generally, the biochemical database provides insights regarding the relationship between various processes and molecules in a biochemical environment. Additionally, because all edges in the bipartite graph connect a molecule node to a process node information retrieval for the purposes of biochemical simulation can be more efficiently accomplished by searching edges in the graph as opposed to searching through nodes in more disorganized graph structure. The bipartite nature of the graph can also be used to quickly identify "dead-end" molecules in a biochemical system. A dead-end molecule may be the product of a process while not being used as a substrate or catalyst in any other reaction, or it may be a substrate of a reaction while not being produced by any other process in the biochemical environment. After identifying dead-end molecules, additional research can be directed to determine how they may be produced or utilized in a biochemical environment. The bipartite graph structure may also be used to prune molecules and process from biochemical environment by traversing the graph from dead-end molecules and eliminating process and molecules that emanate from or contribute to dead-end molecules.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Database Structure

Figure 1:
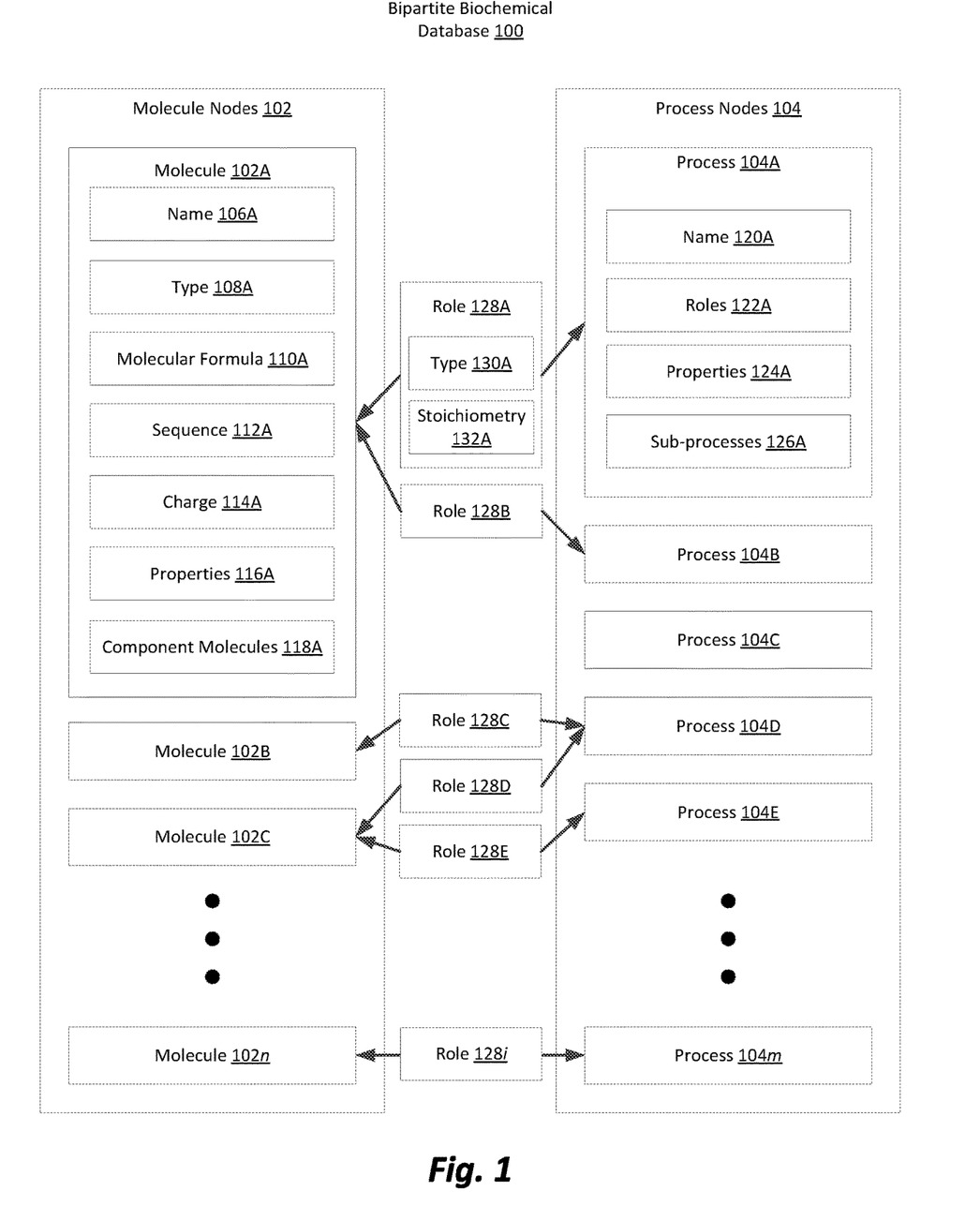
FIG. 1 is a block diagram illustrating a bipartite biochemical database in accordance with one embodiment.

FIG. 1 is a block diagram illustrating a bipartite biochemical database in accordance with one embodiment. The bipartite biochemical database 100 contains data representing the composition and behavior of one or more biochemical environments. Examples of biochemical environments may include, an intracellular environment, the environment in a particular organelle of a cell, an entire cell, intercellular environments or any similar environment found in biology or that might be imagined in a biological simulation. The bipartite nature of the database refers to the two types of database objects or nodes that comprise the database, which may be categorized as "molecule nodes" 102 and "process nodes" 104. Molecule nodes 102 may represent any molecule or other physical particle present in a biochemical environment including atomic elements, ions, compounds, nucleic acids, proteins, and other macromolecules. Process nodes 104 may represent chemical reactions, protein folding, transport, regulatory interactions, active site binding, or any other physical or chemical process that may occur in a biochemical environment. The bipartite biochemical database 100 is organized in a graph structure where the above-mentioned two categories of nodes are connected by edges. Each edge is referred to herein as a "role" 128 and associates a single molecule node 102 with a process node 104, thereby creating a bipartite graph of molecule 102 and process 104 nodes.

A bipartite biochemical database 100 may be implemented using a variety of non-relational database software options. Embodiments utilizing non-relational databases provide advantages in allowing for increased flexibility in the creation of nodes representing biochemical molecules and processes. Biochemical environments typically include molecules of several different types, for example, macromolecules such as nucleic acid chains and proteins in addition to simple compounds such as water and glucose. Due to the diversity in the types of molecules, a non-relational database may be used to allow for documents (e.g. JSON, XML, or other formats) to represent the nodes and edges of the bipartite biochemical database 100. Alternatively, a graph specific database technology such as OrientDB, ArangoDB, AllegroGraph, or any other suitable database framework may be used to implement the bipartite biochemical database 100. Those of skill in the art will appreciate the database structure described herein may be implemented using a variety of available database software options. Additional benefits of the graph structure of the bipartite biochemical database are further described below.

Each molecule node 102 contains molecule metadata fields that provide information about the molecule represented by the node that is pertinent to the behavior of the represented molecule in biochemical environments. These molecule metadata fields may include a molecule name 106, molecule type 108, a molecular formula 110, a molecular sequence 112, a molecular charge 114, molecular properties 116, and component molecules 118. FIG. 1 illustrates molecule nodes 102A, 102B, 102C, through 102n and illustrates the metadata fields 106A, 108A, 110A, 112A, 114A, 116A, and 118A corresponding to molecule node 102A. However, each of the other illustrated molecule nodes 102 may also contain the same, or similar, molecule metadata fields.

A molecule node 102 need not contain data for each of the above metadata fields and, depending on the embodiment, fewer or additional fields may be included in a molecule node 102 as needed for the particular application of the database. In some embodiments, a unique ID may be assigned to each molecule node 102 for easier querying and referencing in the database. Because the various types of molecules found in a biochemical environment vary in their complexity and regimes of interaction with other molecules, different fields may be applicable to each type of molecule. As such, some of the abovementioned fields may be left empty for molecule nodes 102 of a certain type despite being present in the data structure of the molecule node 102.

In some embodiments, the molecule name field 106 of the molecule node 102 contains a human identifiable string indicating the molecule represented by the molecule node 102. The name 106 chosen for a molecule node 102 may be determined by a user entering data into the bipartite biochemical database 100 or it may be automatically generated based on other metadata provided for the molecule. Various naming schemes for biochemical molecules, known to those skilled in the art, may be used to ensure consistency for the name 106 of each molecule node 102.

In some embodiments, the molecule type field 108 indicates the category of molecule to which the represented molecule belongs. The categories are typically set based on the application of the bipartite biochemical database 100 and each molecule may be assigned a type upon entry into the bipartite biochemical database 100. The type field 108 itself may contain a string or type ID number indicating the category to which the molecule represented by the molecule node 102 belongs. Examples of potential categories for a molecule may include, ion, atomic element, compound, organic compound, nucleic acid (DNA, RNA, etc.), amino acid chain, protein, etc. In some embodiments, an application utilizing the bipartite biochemical database 100 may reference the type 108 of a molecule node 102 to determine which properties 116 or other metadata that may be retrieved from the molecule node 102. For example, if the molecule represented by the molecule node 102 has a type 108 indicating that it is a "protein" any application accessing the molecule node 108 may be configured to retrieve protein structure, binding site information, and an amino acid sequence from the properties field 116 of the molecule node 102. In an alternative example, if a molecule node 102 has a type 108 indicating that it is a compound, an application accessing the molecule node may be configured to retrieve a molecular formula, molecular weight, solubility, and/or other information from the molecule node 102.

In some embodiments, the type 108 of a molecule node 102 may indicate the structure of the node itself. For example, the metadata fields present in the molecule node 102 may correspond to the assigned type 108 of the molecule node. For example, the metadata field indicating the sequence of a molecule may only be present in the structure of the node if it has been categorized with the type 108 corresponding to a nucleic acid, amino acid chain, or protein. This could be achieved by requiring an input to the type field 108 when adding a molecule node 102 to the bipartite biochemical database 100 and, when initializing a molecule node 102 in the bipartite biochemical database 100, structure the molecule node 102 based on the received type 108.

In some embodiments, the molecular formula field 110 indicates the molecular or chemical formula of a molecule represented by a molecule node 102. The molecular formula 110 may be a string indicating the atomic elements comprising the represented molecule or, in the case of some types of molecules, may be a string that indicates that the molecular formula is variable or not applicable to the behavior of the molecule in a biochemical environment of interest. In some embodiments, the molecular formula 110 is represented in a standardized format that conforms to specific molecular formula conventions known in the art. In some embodiments, the molecular formula may also indicate the charge of the molecule or have modifiers associated with the string indicating additional details about the molecular structure of the represented molecule. For example, an additional string may be provided indicating the particular isomer of a compound with multiple isomers (in other embodiments, this information is provided in the properties filed 116).

In some embodiments, the sequence field 112 indicates the sequence of a molecule represented by a molecule node 102. Not all types of molecules contain sequence information but the nucleotide sequence of nucleic acid or the amino acid sequence of a protein may be the most biochemically relevant way to describe the molecule. Therefore, sequence information may only be present in the sequence field 112 if the molecule represented by the molecule node is a biopolymer of some kind. The sequence information 112 is typically a string indicating the order of the monomers comprising the represented molecule. The sequence information may use a standard notation corresponding to the type 108 of molecule represented by the molecule node 102. For example, if the molecule node 102 represents a strand of DNA and is labeled as having a type 108 of "DNA" the sequence information 112 would be a string including a sequence of A's, T's, C's, and G's representing adenine, thymine, cytosine, and guanine respectively. In an alternative example, a molecule node 102 representing a protein may include sequence information 112 indicating the amino acid sequence for the protein.

In some embodiments, the charge field 114 indicates the electrical charge of the molecule represented by the molecule node 102. The charge field 114 may be comprised of an integer value of indicating the electrical charge of the molecule. For example, if the molecule node represents a hydrogen ion the charge field 114 would indicate a "1" indicating a positive charge. In some cases, the charge of a molecule may be variable especially if the molecule is a macro molecule and may occur in a number of different states, in which case the charge field 114 would have a value indicating that the charge was variable. In some cases, the charge of a molecule represented by a molecule node 102 may not be applicable to its behavior in a biochemical environment, therefore, in some embodiments, the charge field 114 may contain a string indicating as such.

In some embodiments, the properties field 116 provides information regarding the relevant chemical and physical properties of a molecule represented by a molecule node 102. In some embodiments, the contents of the properties field 116 may be a key-value pair array indicating the relevant property and its corresponding value. The properties listed in the properties field 116 may vary depending on the type of the molecule indicated by the type field 108. Small molecules and compounds, for example, may have properties 116 indicating standard physical properties associated with the represented molecule including, for example, a melting point, molar mass, density, solubility, acidity, enthalpy of formation, or any other relevant chemical and physical property. In some embodiments, the properties field 116 may contain null values for each property that is not known or not relevant to a particular molecule. In larger macromolecules, other properties such as the binding state of a protein, the folding state of the protein, the methylation state of a DNA strand, and other relevant macro molecular properties may be indicated in the properties field 116. Additionally, some properties may be devoted to describing interactions between the represented molecule and other molecules. For example, the active site of a protein or the binding domain of a DNA strand may be described within the properties field 116. In some embodiments, the properties metadata field 116 may also include a three dimensional model of a protein, small molecule interactions of the protein, or pathway information for the molecule. In other embodiments, these properties may be represented in additional metadata fields in a molecule node 102.

In some embodiments, the component molecule field 118 indicates molecules that comprise the molecule represented by a molecule node 102. Component molecules may be any molecule that might contribute to the formation of the represented molecule and they may be represented by a string indicate the names 106 of each component molecule. Some examples include molecules that may occupy a binding site of a protein, nucleotides that comprise a nucleic acid, components of a molecular compound, conjugate bases of a particular acid, etc. The component molecule field 118 may include a list of strings indicating the component molecules or, in some embodiments a list of unique ID numbers indicating the component molecules.

FIG. 1 illustrates a number of molecule nodes 102A, 102B, 102C, through 102n and depending on the database technology used can be extended to include any number of molecule nodes 102, as needed for the application of the bipartite biochemical database 100.

In addition the molecule nodes 102, the bipartite biochemical database 100 also includes process nodes 104. As previously described, process nodes 104 may describe any type of physical or chemical process that may occur in a biochemical environment. Each process node 104 contains process metadata fields describing the process represented by the process node 104, including but not limited to a process name 120, roles in the process 122, properties of the process 124, and sub-processes of the process 126. Like the molecule nodes 102 in the bipartite biochemical database 100, depending on the particular process being represented, the process metadata fields of the process node 104 may be empty where the metadata of the field would not be applicable.

In some embodiments, the name metadata field 120 contains a human recognizable string identifying the process represented by the process node. Like the name field 106 of the molecule node 102, in some embodiments, an ID number for the process may be included in addition to the name 120 of the process node 120. In some embodiments, the name 120 or corresponding unique ID may be used as a reference to the associated process node 120 in the bipartite biochemical database 100.

In some embodiments, process nodes 104 include a role metadata field 122, which lists the roles of molecules in the process represented by the process node 104. Processes that occur in biochemical environments operate on at least one molecule or other element in that environment. However, not all molecules involved in a process necessarily have the same "role" in that process. For example, most chemical reactions have a set of substrate molecules needed to initiate the reaction and a set of products that are generated as a result of the reaction. Thus, molecules that are associated with a process are characterized based on the role of the associated molecule in the process. In some embodiments, the following classifications of roles may be included in the bipartite biochemical database: substrate/reactant, catalyst, product, or cofactor. In embodiments that include process nodes 104 that represent physical processes, the same molecule may be included in multiple roles. For example, if a process node 104 represents the transportation of a protein from the endoplasmic reticulum of a cell to the Golgi apparatus the role field 122 might have two roles including a "departing molecule" and a "destination molecule." Each of these two roles would be satisfied by the same molecule, though the molecule might be represented by two separate molecule nodes 102 each representing the molecule in a different location in the cell. Embodiments that include physical processes represented as process nodes 104 may enable applications utilizing the bipartite biochemical database 100 to create more detailed simulations of a biochemical environment, which account for both chemical and physical transitions of the molecules found in the biochemical environment. Additionally, it is also possible for a molecule to play multiple roles in the same process. For example, a protein may be both a substrate and a catalyst in certain processes. In these cases, two roles may be created for the same molecule in a process node 104.

The structure of the data in the role field 122 may be an array including pairs of strings identifying the type of role and the molecule that satisfies that role in the represented process. In other embodiments, other data structures known in the art may be used to store the same information. The role metadata field may reference a molecule node 102 representing the molecule listed in the role field 104. Alternatively, the role field 122 may include references to role edges 128 that represent roles played by molecules in processes of the bipartite biochemical database 100.

In some embodiments, the process properties field 124 lists properties of the process represented by the process node 104. Processes that occur in a biochemical environment have a variety of properties that may be of interest for the purpose of simulation or data collection. Thus, the bipartite biochemical database 100 may store properties in an array or other data structure in the properties field 124 of a process node 104. In the case of chemical reactions, activation energy, Gibbs free energy change, kinematic properties and other thermodynamic properties known in the art may be included in the properties field 124. For physical processes, which may include protein folding operations and the movement of molecules in an intracellular environment in addition to any other physical process that may occur in a biochemical environment may be listed in the properties field 124.

In some embodiments, the sub-process field 126 stores sub-processes of the process represented by the process node 104. Many processes that occur in a biochemical environment may occur in multiple steps. Especially for the purpose of reaction rate determination (through identification of a rate limiting step) it is useful to maintain information of sub-process comprising a process represented by a process node 104. The sub-processes 126 may be referenced by a name 120 or unique ID number and will typically have a separate node in the bipartite biochemical database.

In some embodiments, the two types of nodes in the bipartite biochemical database 100 are associated with each other using edges, referred to herein as "roles" 128, that represent the role an associated molecule plays in an associated process. The roles 128 themselves may be structured such that they contain direct pointers to the associated molecule node 102 and the associated process node 104. In addition to containing pointers to the associated molecule node 102 and the associated process node 104, the role object 128 may also contain metadata indicating the type of role 130 that the molecule represented by the associated molecule node 102 plays in the process represented by the associated process node 104. Additionally, the role 128 contains the stoichiometry value of the represented molecule in the represented process. These edges 128 ensure that in applications involving the simulation of a biochemical environment accurate stoichiometric relationships are maintained in each reaction. In some embodiments, roles 128 may have a defined directionality in the graph. The directionality may indicate whether the molecule represented by the associated molecule node 102 is being consumed or produced in the process represented by the associated process node 104. The directionality of a role 128 in the bipartite biochemical database may be related to the role type described below. In embodiments with role directionality, mathematic techniques utilizing directed graphs can be utilized by applications utilizing the bipartite biochemical database.

As previously described with respect to the roles field 122 in the process node 104, the roles type 130 may be one of substrate/reactant, catalyst, product, or cofactor for chemical processes and may be any applicable role in a physical process that would accurately described the behavior of the associated molecule in the associated physical process. The role type 130 may be stored as a string describing the role type or by any other effective means known in the art. In embodiments utilizing a directed graph, the directionality of a role 128 may correspond to the role type 130. For example, a role type 130 of substrate/reactant would result in a directionality from the associated molecule node 102 to the associated process node 104 while a role type 130 of product would result in a directionality flowing from the associated process node 104 to the associated molecule node 102. Other role types 130 such as catalyst or cofactor may corresponding a bidirectional role edge 128 because the molecule represented by the molecule node 102 remains present before and after the associated process occurs.

In some embodiments, the stoichiometric coefficient metadata field 132 stores the stoichiometric coefficient of the associated molecule in the associated process. The stoichiometric coefficient indicates the ratio of each molecule having a role in a particular process and provides a framework for determining the flux of molecules in a biochemical environment. The stoichiometric coefficient 132 of a role 128 may be indicated by a positive integer equal to the value of the stoichiometric coefficient in a chemical equation representing the process associated with the role 128. For physical processes, the stoichiometric coefficient may instead be based on whatever physical interaction between molecules is being represented by the associated process.

FIG. 1 illustrates n molecule nodes 102 including molecule nodes 102A, 102B, 102C, m process nodes 104 including process nodes 104A, 104B, 104C, 104D, and 104E, and i role edges 128 including 128A, 128B, 128C, 128D, and 128E. This illustrates that there may be differing numbers of molecule nodes 102, process nodes 104, and role edges 128 and that there need not be a one to one matching of molecule nodes 102 to process nodes 104. Additionally, as demonstrated by the arrows illustrating example connections between molecule nodes 102, roles 128, and process nodes 104, a molecule node 102 may be associated with multiple process nodes 104 and vice versa. For example, molecule node 102A is illustrated as being connected to both process node 104A and process node 104B through roles edges 128A and 128B respectively. Thus, based on the illustrated mapping, the molecule represented by molecule node 102A is involved in the processes represented by both process nodes 104A and 104B.

II. Examples

Figure 2:
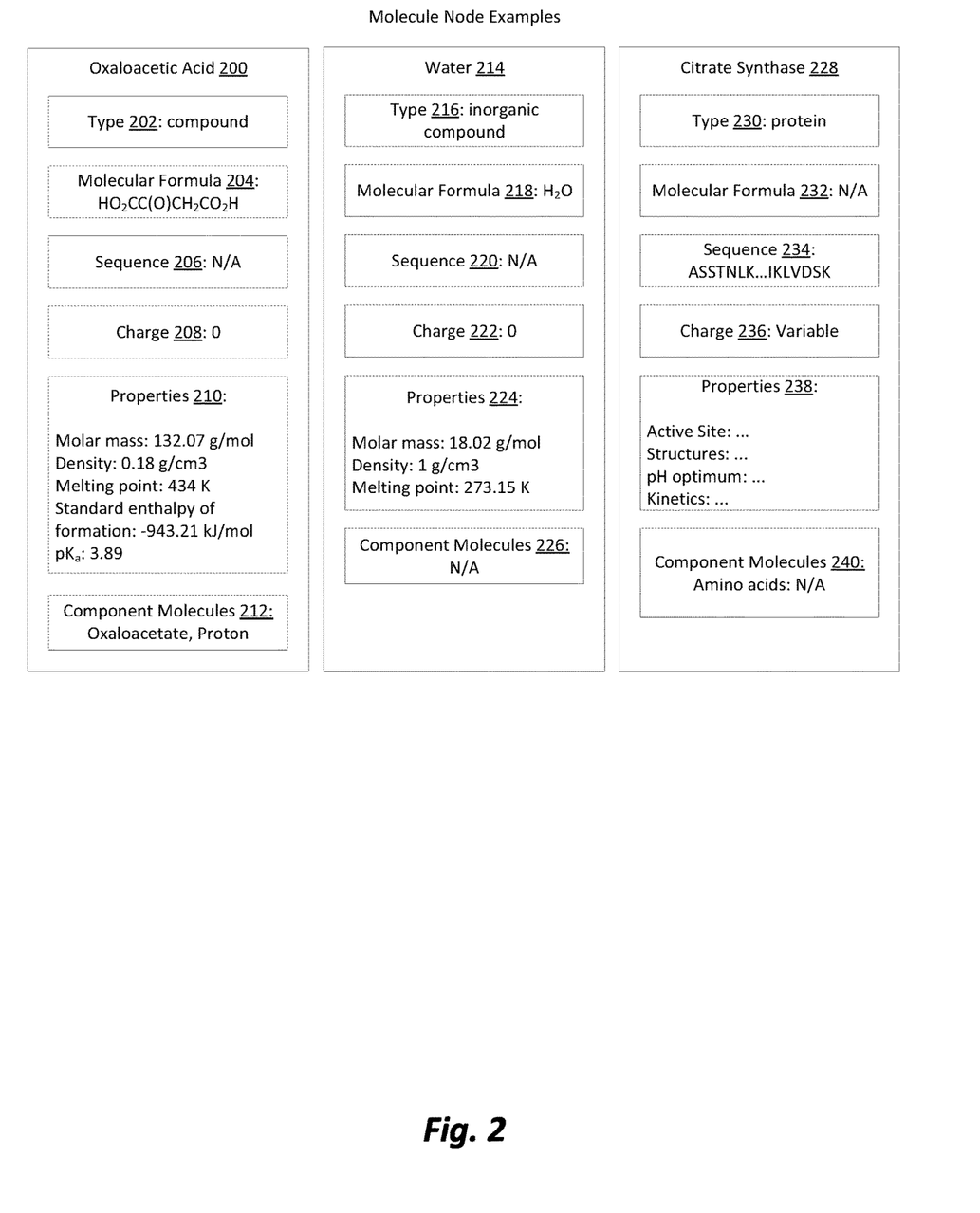
FIG. 2 is a block diagram illustrating examples of molecule nodes in accordance with one embodiment.
Figure 3:
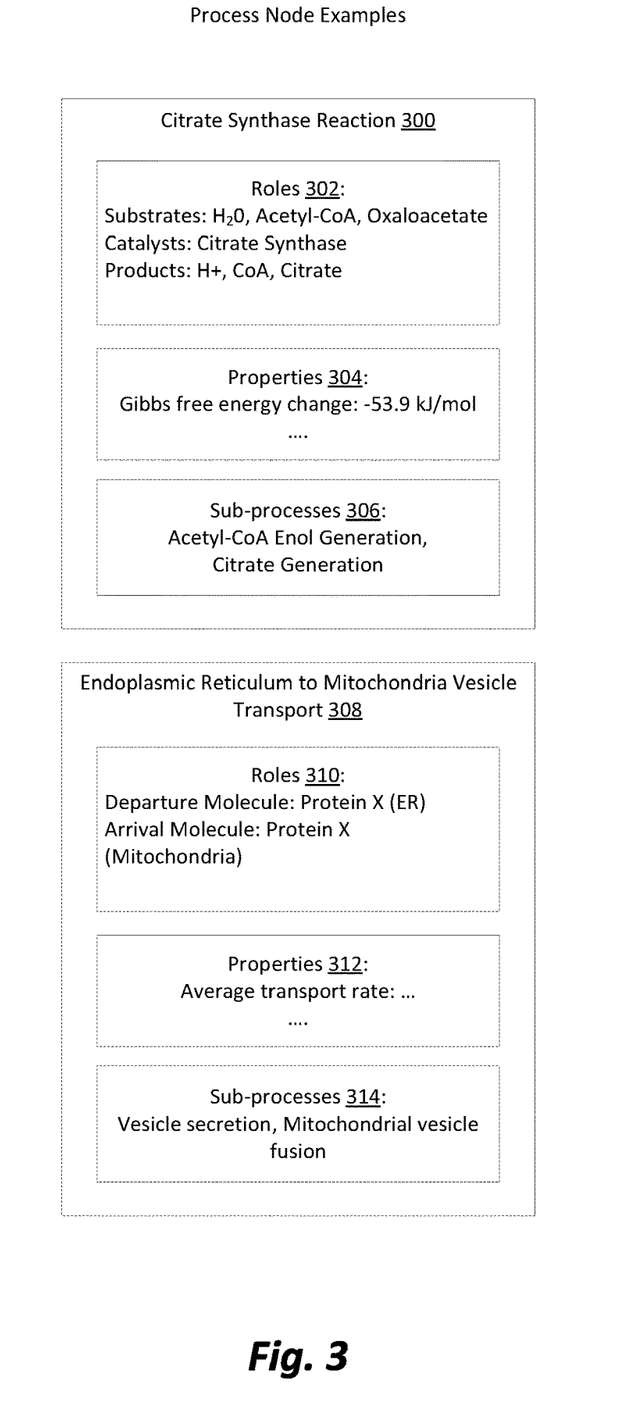
FIG. 3 is a block diagram illustrating an examples of process nodes in accordance with one embodiment.
Figure 4:
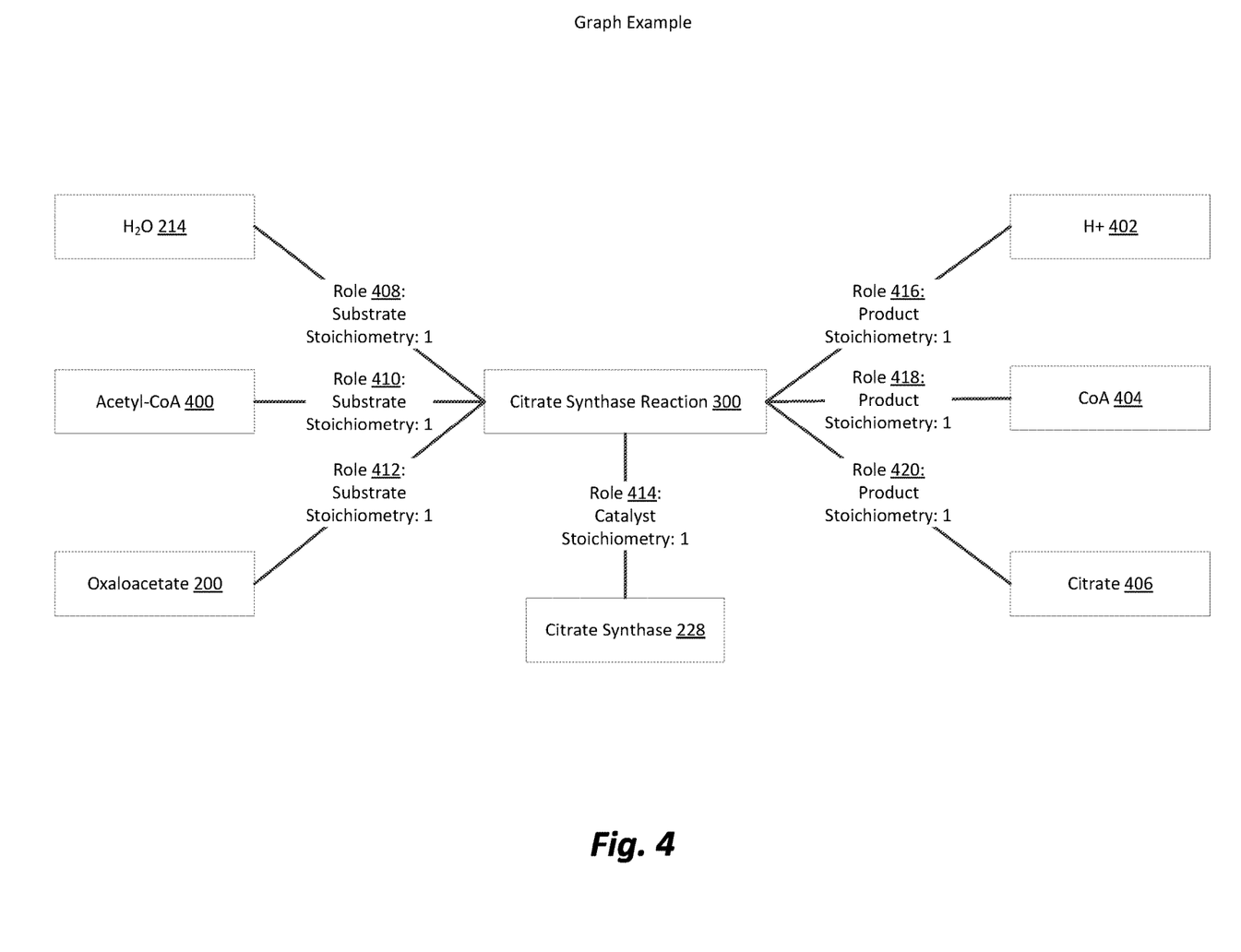
FIG. 4 is a block diagram illustrating nodes and edges included in an example biochemical reaction in accordance with one embodiment.

FIGS. 2-4 illustrate possible implementations of the above described bipartite biochemical database 100. Each of the illustrated examples shows just one possible implementation of the bipartite biochemical database and are simplified for the purposes of discussion herein. For instance, in some embodiments, additional biochemical data would be available and would be stored as metadata. In other embodiments, more complex data such as 3D models representing protein structure or other macromolecular behaviors may be stored in the bipartite biochemical database 100 that are not shown in the following examples. The text as illustrated in the figures may represent data stored in a variety of possible databases formats and may be representative of more complex data structure than as they appear in FIGS. 2-4.

FIG. 2 is a block diagram illustrating examples of molecule nodes in accordance with one embodiment. FIG. 2 illustrates three examples of molecule nodes 102 in the above described bipartite biochemical database 100, including nodes representing oxaloacetic acid 200, water 214, and citrate synthase 228.

The oxaloacetic acid node 200 has types 108 "compound," 202 thereby indicating that oxaloacetic acid is a compound (when not in an aqueous solution where it may disassociate into a conjugate base, oxaloacetate, and protons). The molecular formula field 110 of the node contains the string "$HO_2CC(O)CH_2CO_2H$" which indicates the composition of oxaloacetic acid. The sequence metadata field 112 of the oxaloacetic acid node 200 would be represented by a null value 206 or a representative string indicating that there are no sequence data for oxaloacetic acid. In an alternate embodiment, the sequence field 112 may be not be present in molecule nodes 102 having a type "compound." The charge field 114 of the oxaloacetic acid node 200 stores the value "0" 210 indicating that oxaloacetic acid has a neutral charge. The properties field 116 of the oxaloacetic acid node 200, includes a number of values 210 of various chemical and physical properties of oxaloacetic acid including a molar mass of 132.07 g/mol, a density of 0.18 g/mol, a melting point of 434 K, a standard enthalpy of formation of −943.21 kJ/mol, and a $pK_a$ of 3.89. In some embodiments, the properties field 116 may include additional properties of oxaloacetic acid. The component molecule field 118 of the oxaloacetic acid node 200 contains the strings "oxaloacetate ion" and "proton" indicating that these to molecules a components in oxaloacetic acid.

In an additional example, a molecule node 102 represents water ($H_2O$). In this example, the name 106 of the node may simply be "water." The type 108 for water, in this example, is "inorganic compound" 216, indicating that water is an inorganic compound. The molecular formula 110 for water is "$H_2O$" 218. As in the case, of oxaloacetate, no sequence information 112 is stored in the sequence field of the water node 214. The charge field 114 indicates a value 222 of zero and the properties field 116 stores physical properties of water 224 including a molar mass of 18.02 g/mol, a density of 1 g/mol, and a melting point of 273.15 K. In some embodiments, additional data may be stored in the properties field indicating how the physical properties of a molecule may change in different temperature and pressure conditions. The component molecule field 118 contains strings or other data 226 representing hydrogen and oxygen.

In an additional example, FIG. 2 illustrates a molecule node 102 representing citrate synthase 228. The name 106 of the molecule node 102 in this case would "Citrate Synthase" or some other recognizable string identifying the molecule. The type 108 of the citrate synthase node would be "protein" 230 and in some embodiments may also indicate the folding state of the protein. The molecular formula field 110 of the citrate synthase contains a null value 232 or a string representing that fact that the molecular formula of the protein is not applicable or useful to its behavior in a biochemical environment. However, the sequence field 112 contains a string 234 representing the amino acid sequence of the protein. The charge field 114 of the citrate synthase node 228 indicates that the charge of the protein 236 is variable depending on the isoelectric point and the pH of the environment. In some embodiments, the information on the isoelectric point of a protein may be stored in the charge field 114 if the information is available. The properties field 116 of the citrate synthase node 238 describes the structure of the protein and kinetic properties of the protein numerically, categorically or through the use of 3D models and other methods of describing protein structure and kinetics known in the art. The component molecule field 118 of the citrate synthase node indicates the amino acids that comprise the citrate synthase protein 240.

FIG. 3 is a block diagram illustrating an examples of process nodes in accordance with one embodiment. FIG. 3 illustrates two example process nodes 104, a citrate synthase reaction node 300, and a vesicle transport node 308. The citrate synthase reaction node 300 represents the chemical process of synthesizing citrate while the vesicle transport node 308 represents a physical process of moving an unspecified protein from one location to another in a cellular environment.

The roles metadata field 122 of the citrate synthase reaction node 300 stores data 302 describing the substrates, catalyst, and products of the citrate synthase reaction, thereby listing $H_2O$, Acetyl-CoA, and oxaloacetate as substrates, citrate synthase as a catalyst, and the products as $H^+$, CoA, and citrate. This data indicates the molecule nodes 102 that are associated with the citrate synthase reaction node 300 through role edges 128. The properties field 124 of the citrase synthase reaction node 300 includes the Gibbs free energy change of the reaction and may include other details regarding the reaction kinetics or experimental rate data. The sub-processes metadata field 126 of the citrate synthase reaction node 300 indicates any sub-processes that might comprise the citrate synthase reaction. The sub-process field 126 indicates that "acetyl-CoA enol generation" and "citrate generation" are sub-processes of the citrate synthase reaction. In some embodiments, the sub-process field 126 may contain direct links to the sub-processes stored therein.

The role field 122 of the vesicle transport node 308 indicates that because the process being represented by the node is a physical process, the same molecule plays both of the roles since no chemical changes occur. However, in embodiments where physical processes are included in the bipartite biochemical database 100, separate molecule nodes 102 may be assigned to the same molecule to represent different physical states of that molecule. For example, although the same protein satisfies both roles of the citrate synthase reaction node 308, "protein X," there may be two molecule nodes 102 representing protein X. One representing protein X in the endoplasmic reticulum, "protein X ER," and the other representing protein X in the mitochondria "protein X mitochondria." The properties field 124 of the a process node representing the vesicle transportation process contains rate information 312 pertaining to the transportation of the protein from the endoplasmic reticulum to the mitochondria. In other embodiments, additional information about a physical process may be included. The sub-process field 126 of the vesicle transport node 308 includes sub-processes representing vesicle secretion at the endoplasmic reticulum and vesicle fusion at the mitochondria.

FIG. 4 is a block diagram illustrating nodes and edges included in an example biochemical reaction in accordance with one embodiment. FIG. 4 illustrates a small section of a graph that might comprise a bipartite biochemical database 100. Specifically FIG. 4 illustrates the molecule nodes 102 and process node 104 that are associated with the citrate synthase reaction. FIG. 4 illustrates seven molecule nodes $H_2O$ 214, Acetyl-CoA 400, oxaloacetate 200, $H^+$ 402, CoA 404, citrate 406, and citrate synthase 228. These molecule nodes 102 are associated with the citrate synthase reaction process node 300 with role edges 408, 410, 412, 416, 418, 420, and 414 respectively. Each of the edges defines the role of each molecule represented by the molecule nodes 102 in the citrate synthase reaction.

III. Advantages of Bipartite Database Structure

The bipartite biochemical database structure 100 offers many advantages with regards to the simulation and understanding of biochemical environments. The graph based structure comprised of edges using direct pointers allows for the quick transversal of the graph. Thus, when a biochemical environment is described in terms of its molecular composition, the bipartite biochemical database can be used to determine the chemical and physical processes that might occur in that environment by quickly traversing the graph starting from the identified molecules in the biochemical environment. Alternatively, if a set of processes are to be simulated the set of molecules involved in those processes can be identified through a graph traversal starting at the processes to be simulated.

Figure 5:
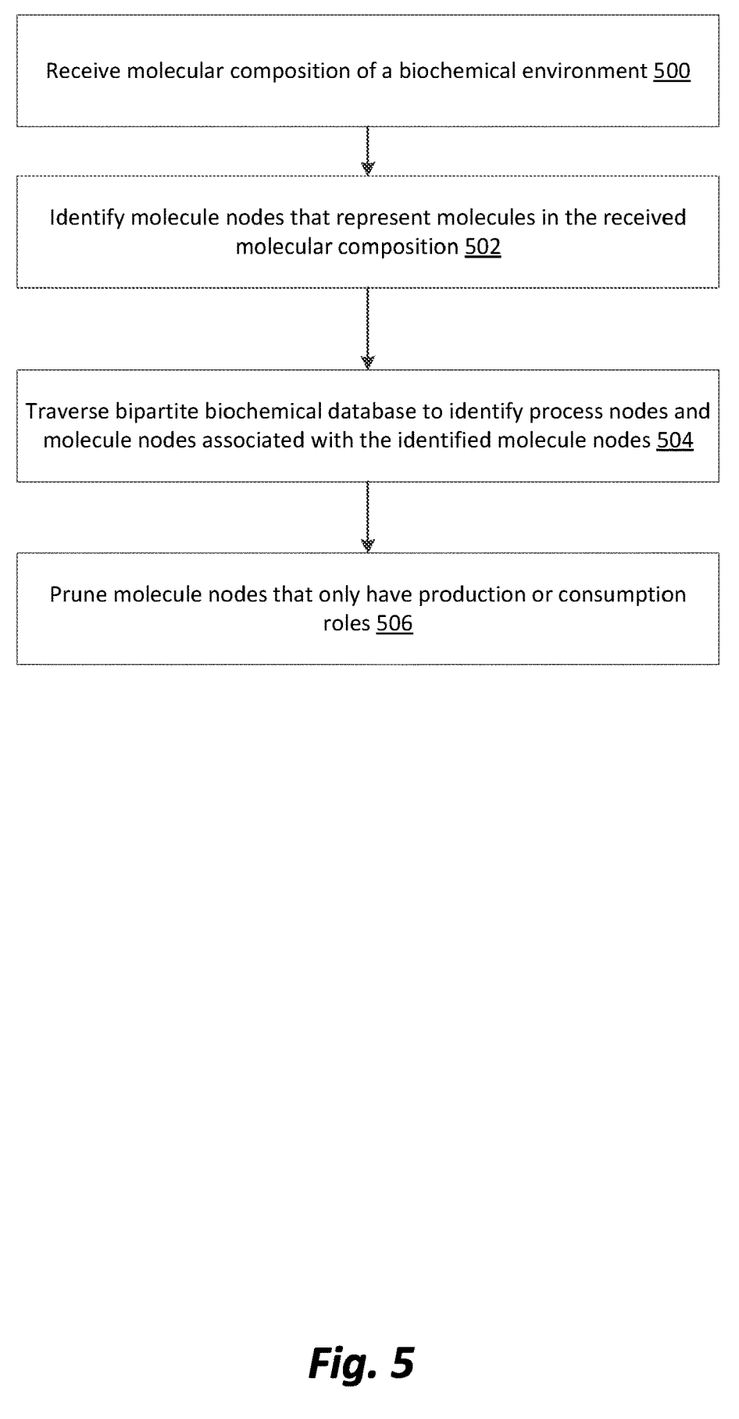
FIG. 5 is a flow diagram illustrating a method of identifying processes that may occur in a biochemical environment in accordance with one embodiment.

FIG. 5 is a flow diagram illustrating a method of identifying processes that may occur in a biochemical environment in accordance with one embodiment. The method illustrated in FIG. 5 may be completed by one or more processors configured with instructions to carry out the illustrated steps by leveraging the bipartite biochemical database 100.

The illustrated method of identifying processes occurring in a biochemical environment utilizing the bipartite biochemical database 100 begins by receiving 500 a molecular composition of a biochemical environment. The molecular composition may be determined through experimental processes or created as a hypothetical environment for simulation. The received composition data may be comprised of a list of molecule names 106 or unique. The bipartite biochemical database 100 is then used to identify 502 molecule nodes 102 that represent the molecules in the received molecular composition. If the molecular composition data is received in the form of a list of names 106 then identification can be completed by querying the bipartite biochemical database 100 for the list names 106. In some embodiments, further processing may be required to identify the molecule nodes 102 that represent the received molecular composition data. In some embodiments, the application utilizing the bipartite biochemical database 100 will notify a user of molecules not represented in the bipartite biochemical database 100 but have been received in the molecular composition data. Upon notification of missing molecular nodes, nodes representing the molecules may be added to the bipartite biochemical database 100.

Once a set of molecule nodes 102 have been identified the bipartite biochemical database is identifies 504 additional molecules or processes 1 by traversing the biochemical database 102. The bipartite biochemical database 100 is a directed graph, the traversal of the graph would follow the directionality of the roles 128. Alternatively, process nodes 104 are not identified as associated with the identified set of molecule nodes 102 unless all of the product/reactant roles of the process are filed by one of the identified molecule nodes 102. The additional molecule nodes identified in the graph traversal (as opposed to being received in the molecular composition data) may be transitional molecules between sub-processes not included in the received molecular composition data. These additional molecular may inform researchers of additional molecules that may be present in a biochemical environment that were not previously detected. One of skill in the art will recognize that many graph traversal algorithms may be used to achieve step 504, including both breadth first search or depth first search, depending on the embodiment.

After traversing 504 the bipartite biochemical database 100 to identify process nodes 104 and addition molecule nodes 102, "dead-end" molecule nodes may be pruned 506 from the identify set of nodes, depending on the embodiment. "Dead-end" nodes are molecule nodes 102 that have no identified processes for which they are a reactant/substrate or have no identified processes for which they are a product. Physically, these dead-end molecules could not possibly accumulate or be consumed without an additional processes that are not present in the database or are not possible. For these reasons, these molecules are pruned from the identified molecule nodes 102, and depending on the embodiment may be identified for further research. In some embodiments, the pruning process 506 may be recursive in that after the first set of dead-end molecules nodes have been removed from the identified set, the recursive processes determines if any process nodes are left without all of the associated roles occupied. If any processes are identified then they are pruned from the identified set as well, which would cause the recursive process to continue to a next step of pruning dead-end molecule nodes.

After the pruning process is complete, the result is an identified subset of molecules nodes 102 and process nodes 104 from the larger set of all nodes in the database that represent the processes and molecules that would be present in a biochemical environment that has a molecular composition indicated by the received molecular composition data. These identified processes and molecules may then be utilized for simulation or for further research on the biochemical environment.

One of skill in the art will appreciate that a similar method may be implemented to identify a set of molecules that would be hypothetically necessary to achieve a received set of biochemical processes. In this case, the graph traversal would instead begin at a set of received process nodes 104 as opposed to a set of received molecule nodes 102.

IV. Additional Considerations

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof. In one embodiment, a software module is implemented with a computer program product comprising a persistent computer-readable medium containing computer program code, which can be executed by a computer processor for performing any or all of the steps, operations, or processes described.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, an example of which is set forth in the following claims.

What is claimed is:

1. A system for storing biochemical information comprising:
   a non-transitory computer readable storage medium;
   a processor executing instructions to configure the non-transitory computer readable storage medium to store a database structured as a bipartite graph comprising: a plurality of molecule nodes, wherein each molecule node of the plurality of molecule nodes represents a molecule in a biochemical environment and wherein each molecule node of the plurality of molecule nodes includes a plurality of molecule metadata fields characterizing the molecule;
   a plurality of process nodes, wherein each process node of the plurality of process nodes represents a process occurring in a biochemical environment, and wherein each process node of the plurality of process nodes includes a plurality of process metadata fields including at least a roles field, wherein the roles field defines a set of roles of molecules in the process; and
   a plurality of edges, wherein each edge of the plurality of edges associates a molecule node to a process node, and wherein each edge of the plurality of edges characterizes a role of a molecule represented by the associated molecule node in a process represented by the associated process node, wherein the edge includes the stoichiometric coefficient of the molecule in the process;
   wherein, for each edge of one or more first edges of the plurality of edges, the role characterized by the edge is a catalyst role or cofactor role and a directionality of the edge is bidirectional; wherein, for each edge of one or more second edges of the plurality of edges, the role characterized by the edge is a reactant role and a directionality of the edge is unidirectional; and wherein the plurality of molecule nodes, the plurality of process nodes, and the plurality of edges are stored in a non-SQL graph database.

2. The system of claim 1, wherein the molecule metadata fields include at least a molecule composition field.

3. The system of claim 1, wherein the molecule metadata fields include one or more of:
   a molecule name field,
   a molecule type field,
   a molecular formula field,
   a sequence field,
   a charge field,
   a molecular properties field, or
   a component molecules field.

4. The system of claim 1, wherein, for a particular edge of the plurality of edges, the edge characterizes multiple roles for a connected molecule node, the multiple roles including a substrate role and another role.

5. The system of claim 1, wherein one or more of the plurality of molecule nodes represents a single molecule in one or more physical settings.

6. The system of claim 1, wherein the plurality of process nodes represent chemical and physical processes.

7. A non-transitory computer readable storage medium storing instructions to configure a database structured as a bipartite graph comprising;
   a plurality of molecule nodes, wherein each molecule node of the plurality of molecule nodes represents a molecule in a biochemical environment and wherein each molecule node of the plurality of molecule nodes includes a plurality of molecule metadata fields characterizing the molecule;
   a plurality of process nodes, wherein each process node of the plurality of process nodes represents a process occurring in a biochemical environment, and wherein each process node of the plurality of process nodes includes a plurality of process metadata fields including at least a roles field, wherein the roles field defines a set of roles of molecules in the process; and
   a plurality of edges, wherein each edge of the plurality of edges associates a molecule node to a process node, and wherein each edge of the plurality of edges characterizes a role of a molecule represented by the associated molecule node in a process represented by the associated process node, wherein the edge includes the stoichiometric coefficient of the molecule in the process;
   wherein, for each edge of one or more first edges of the plurality of edges, the role characterized by the edge is a catalyst role or cofactor role and a directionality of the edge is bidirectional; wherein, for each edge of one or more second edges of the plurality of edges, the role characterized by the edge is a reactant role and a directionality of the edge is unidirectional; and wherein the plurality of molecule nodes, the plurality of process nodes, and the plurality of edges are stored in a non-SQL graph database.

8. The non-transitory computer readable storage medium of claim 7, wherein the molecule metadata fields include at least a molecule composition field.

9. The non-transitory computer readable storage medium of claim 7, wherein the molecule metadata fields include one or more of:
   a molecule name field,
   a molecule type field,
   a molecular formula field,
   a sequence field,
   a charge field,
   a molecular properties field, or
   a component molecules field.

10. The non-transitory computer readable storage medium of claim 7, wherein, for a particular edge of the plurality of edges, the edge characterizes multiple roles for a connected molecule node, the multiple roles including a substrate role and another role.

11. The non-transitory computer readable storage medium of claim 7, wherein one or more of the plurality of molecule nodes represents a single molecule in one or more physical settings.

12. The non-transitory computer readable storage medium of claim 7, wherein the plurality of process nodes represent chemical and physical processes.

13. A method comprising: configuring a database structured as a bipartite graph comprising:
   a plurality of molecule nodes, wherein each molecule node of the plurality of molecule nodes represents a molecule in a biochemical environment and wherein each molecule node of the plurality of molecule nodes includes a plurality of molecule metadata fields characterizing the molecule;

a plurality of process nodes, wherein each process node of the plurality of process nodes represents a process occurring in a biochemical environment, and wherein each process node of the plurality of process nodes includes a plurality of process metadata fields including at least a roles field, wherein the roles field defines a set of roles of molecules in the process; and a plurality of edges, wherein each edge of the plurality of edges associates a molecule node to a process node, and wherein each edge of the plurality of edges characterizes a role of a molecule represented by the associated molecule node in a process represented by the associated process node, wherein the edge includes the stoichiometric coefficient of the molecule in the process;

wherein, for each edge of one or more first edges of the plurality of edges, the role characterized by the edge is a catalyst role or cofactor role and a directionality of the edge is bidirectional; wherein, for each edge of one or more second edges of the plurality of edges, the role characterized by the edge is a reactant role and a directionality of the edge is unidirectional; and wherein the plurality of molecule nodes, the plurality of process nodes, and the plurality of edges are stored in a non-SQL graph database.

14. The method of claim 13, wherein the molecule metadata fields include at least a molecule composition field.

15. The method of claim 13, wherein the molecule metadata fields include one or more of:
a molecule name field,
a molecule type field,
a molecular formula field,
a sequence field,
a charge field,
a molecular properties field, or
a component molecules field.

16. The method of claim 13, wherein, for a particular edge of the plurality of edges, the edge characterizes multiple roles for a connected molecule node, the multiple roles including a substrate role and another role.

17. The method of claim 13, wherein one or more of the plurality of molecule nodes represents a single molecule in one or more physical settings.

18. The method of claim 13, wherein the plurality of process nodes represent chemical and physical processes.

19. The method of claim 13, further comprising:
using the database structured as a bipartite graph to identify one or more dead-end molecules represented by a subset of the plurality of molecule nodes, wherein, for each of the one or more dead-end molecules, a subset of edges of the plurality of edges that are connected to the molecule node in the subset representing the dead-end molecule indicates that:
the dead-end molecule is not used as a reactant, substrate or catalyst by any of the processes represented by the plurality of process nodes; or
the dead-end molecule is not produced by any of the processes represented by the plurality of process nodes;
pruning the subset of the plurality of molecule nodes from the bipartite graph; and
performing a simulation of a biochemical environment using the pruned bipartite graph.

* * * * *